(12) United States Patent
Riano et al.

(10) Patent No.: US 11,510,790 B2
(45) Date of Patent: Nov. 29, 2022

(54) TRIANGULAR FIBROCARTILAGE COMPLEX RECONSTRUCTION TECHNIQUES

(71) Applicant: ARTHREX, INC., Naples, FL (US)

(72) Inventors: Felix Riano, Naples, FL (US); Christopher Adams, Naples, FL (US)

(73) Assignee: ARTHREX, INC., Naples, FL (US)

( * ) Notice: Subject to any disclaimer, the term of this patent is extended or adjusted under 35 U.S.C. 154(b) by 693 days.

(21) Appl. No.: 16/561,185

(22) Filed: Sep. 5, 2019

(65) Prior Publication Data

US 2021/0068984 A1  Mar. 11, 2021

(51) Int. Cl.
| | |
|---|---|
| A61F 2/46 | (2006.01) |
| A61F 2/30 | (2006.01) |
| A61B 17/04 | (2006.01) |
| A61L 27/36 | (2006.01) |
| A61B 17/17 | (2006.01) |

(52) U.S. Cl.
CPC ........ *A61F 2/4618* (2013.01); *A61B 17/0401* (2013.01); *A61B 17/1782* (2016.11); *A61B 17/1796* (2013.01); *A61F 2/30749* (2013.01); *A61F 2/30756* (2013.01); *A61F 2/4657* (2013.01); *A61L 27/3633* (2013.01); *A61B 2017/0414* (2013.01); *A61B 2017/0464* (2013.01); *A61F 2002/30751* (2013.01); *A61F 2002/30757* (2013.01); *A61F 2002/4658* (2013.01); *A61F 2002/4677* (2013.01)

(58) Field of Classification Search
None
See application file for complete search history.

(56) References Cited

U.S. PATENT DOCUMENTS

| | | | | |
|---|---|---|---|---|
| 6,140,452 | A * | 10/2000 | Felt | C08G 18/69 528/65 |
| 9,468,433 | B2 * | 10/2016 | Denham | A61B 17/06166 |
| 9,788,876 | B2 * | 10/2017 | Stone | A61B 17/0401 |
| 10,004,588 | B2 * | 6/2018 | Berelsman | A61B 17/0401 |
| 10,172,703 | B2 | 1/2019 | Adams et al. | |
| 2004/0073227 | A1 * | 4/2004 | Dreyfuss | A61B 17/1778 606/96 |
| 2005/0192632 | A1 * | 9/2005 | Geissler | A61F 2/0811 606/232 |
| 2007/0190108 | A1 * | 8/2007 | Datta | A61L 27/48 424/423 |
| 2009/0138029 | A1 * | 5/2009 | Saliman | A61B 17/0469 606/139 |
| 2009/0228104 | A1 * | 9/2009 | Strzepa | A61F 2/30756 623/14.12 |
| 2010/0087879 | A1 * | 4/2010 | Vanasse | A61F 2/4261 606/86 R |
| 2017/0095324 | A1 * | 4/2017 | Adams | A61B 17/3423 |
| 2019/0076257 | A1 * | 3/2019 | Dee | A61B 17/1615 |

FOREIGN PATENT DOCUMENTS

CA          3058726 A1 *  11/2018

* cited by examiner

Primary Examiner — Jennifer Dieterle
Assistant Examiner — Melissa A Hoban
(74) *Attorney, Agent, or Firm* — Carlson, Gaskey & Olds, P.C.

(57) ABSTRACT

This disclosure is directed to methods for reconstructing an unstable triangular fibrocartilage complex (TFCC). Exemplary methods include preparing, delivering, and fixating a graft within a distal radioulnar joint in a manner that restores the functionality to the TFCC, thereby improving the joint kinematics of the radioulnar joint.

20 Claims, 17 Drawing Sheets

TRIANGULAR FIBROCARTILAGE COMPLEX RECONSTRUCTION TECHNIQUES

BACKGROUND

This disclosure relates to methods for reconstructing an unstable triangular fibrocartilage complex of a wrist.

The triangular fibrocartilage complex (TFCC) is a group of tissue structures that stabilize the distal radioulnar joint of the wrist. The distal radioulnar joint can become unstable in response to trauma or degenerative conditions that affect the TFCC. Known TFCC reconstruction techniques are complex and do not consistently achieve positive patient outcomes.

SUMMARY

This disclosure is directed to methods for reconstructing an unstable triangular fibrocartilage complex (TFCC). Exemplary methods include preparing, delivering, and fixating a graft within a distal radioulnar joint in a manner that restores the functionality to the TFCC, thereby improving the joint kinematics of the radioulnar joint.

A method for reconstructing a triangular fibrocartilage complex (TFCC) of a wrist, according to an exemplary aspect of the present disclosure incudes, among other things, forming a first bone hole near a dorsal corner of an ulnar side of a radius, forming a second bone hole near a volar corner of the ulnar side of the radius, forming a bone tunnel through an ulna, implanting a first suture anchor in the first bone hole, implanting a second suture anchor in the second bone hole, measuring a first dimension of a defect of the TFCC in a dorsal-volar plane, measuring a second dimension of the defect in a radial-ulnar plane, sizing a graft to a size indicated by the first dimension and the second dimension, retrieving a first suture strand from the first suture anchor and a second suture strand from the second suture anchor, passing the first suture strand and the second suture strand through the sized graft with the sized graft located externally from a distal radioulnar joint of the wrist, passing a third suture strand through the sized graft, shuttling the sized graft into the distal radioulnar joint, shuttling the third suture strand through the bone tunnel, fixating the graft to the radius with the first suture strand and the second suture strand, and fixating the graft to the ulna with the third suture strand.

In a further non-limiting embodiment of the foregoing method, the graft is a dermal graft.

In a further non-limiting embodiment of either of the foregoing methods, the dermal graft is an acellular dermal extracellular matrix graft.

In a further non-limiting embodiment of any of the foregoing methods, the first suture anchor and the second suture anchor are knotless suture anchors.

In a further non-limiting embodiment of any of the foregoing methods, the bone tunnel extends from a lateral cortex of the ulna to a fovea of the ulna.

In a further non-limiting embodiment of any of the foregoing methods, forming the bone tunnel through the ulna includes making an incision at a location this is proximal to a styloid process of the ulna, inserting a guidewire through a lateral cortex of the ulna and then through a fovea of the ulna, and over-drilling the guidewire with a drill bit to form the bone tunnel.

In a further non-limiting embodiment of any of the foregoing methods, the measuring is performed with a measuring probe that is inserted through an arthroscopic cannula.

In a further non-limiting embodiment of any of the foregoing methods, sizing the graft includes marking the graft to indicate the first dimension and the second dimension.

In a further non-limiting embodiment of any of the foregoing methods, shuttling the sized graft into the distal radioulnar joint includes loading the first suture strand through a loop of a shuttle suture strand of the first suture anchor, loading the second suture strand through a loop of a shuttle suture strand of the second suture anchor, and toggling the shuttle suture strands, thereby pulling the sized graft into place against the ulnar side of the radius.

In a further non-limiting embodiment of any of the foregoing methods, passing the third suture strand through the sized graft includes connecting the third suture strand to the sized graft via a mattress stitch.

In a further non-limiting embodiment of any of the foregoing methods, the third suture strand is shuttled through the bone tunnel after shuttling the sized graft into the distal radioulnar joint.

In a further non-limiting embodiment of any of the foregoing methods, shuttling the third suture through the bone tunnel includes passing a loop through the bone tunnel in a direction from a lateral cortex of the ulna toward a fovea of the ulna, retrieving the loop and the third suture strand through an arthroscopic cannula, threading the third suture strand through the loop, and pulling the loop and the third suture strand through the bone tunnel in a direction from the fovea toward the lateral cortex.

In a further non-limiting embodiment of any of the foregoing methods, the methods includes fixating the third suture strand at the lateral cortex with a third suture anchor.

In a further non-limiting embodiment of any of the foregoing methods, the third suture anchor is a knotless suture anchor.

In a further non-limiting embodiment of any of the foregoing methods, sizing the graft includes cutting the graft to the size with a scalpel.

A method for reconstructing a triangular fibrocartilage complex (TFCC) of a wrist, according to another exemplary aspect of the present disclosure includes, among other things, measuring a defect of the TFCC, sizing a dermal graft to a size indicated by measuring the defect, shuttling the sized dermal graft into a distal radioulnar joint of the wrist, fixating the sized dermal graft to a radius with a knotless suture anchor, and fixating the graft to an ulna with an additional knotless suture anchor.

The embodiments, examples, and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

This disclosure describes methods for reconstructing portions of a triangular fibrocartilage complex (TFCC). The proposed methods are designed to restore the functionality to damaged portions of the TFCC.

Figure 1:
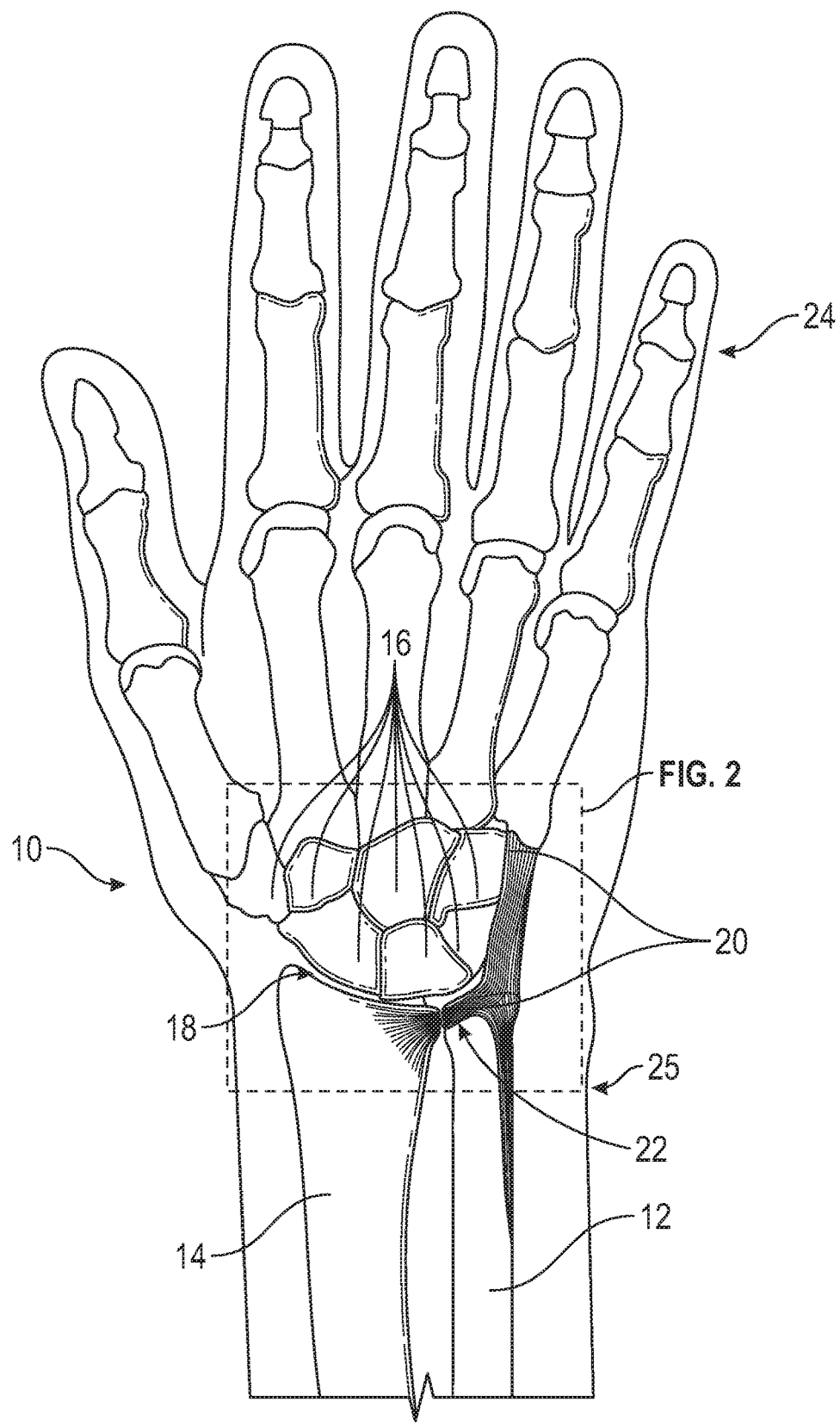
FIG. 1 illustrates a wrist of a human musculoskeletal system.

FIG. 1 illustrates a wrist 10 of a hand 24 of the human musculoskeletal system. The wrist 10 is made up of multiple bones including an ulna 12, a radius 14, and a plurality of carpal bones 16. The ulna 12 and the radius 14 may articulate relative to the carpal bones 16 at a radiocarpal joint 18.

Figure 2:
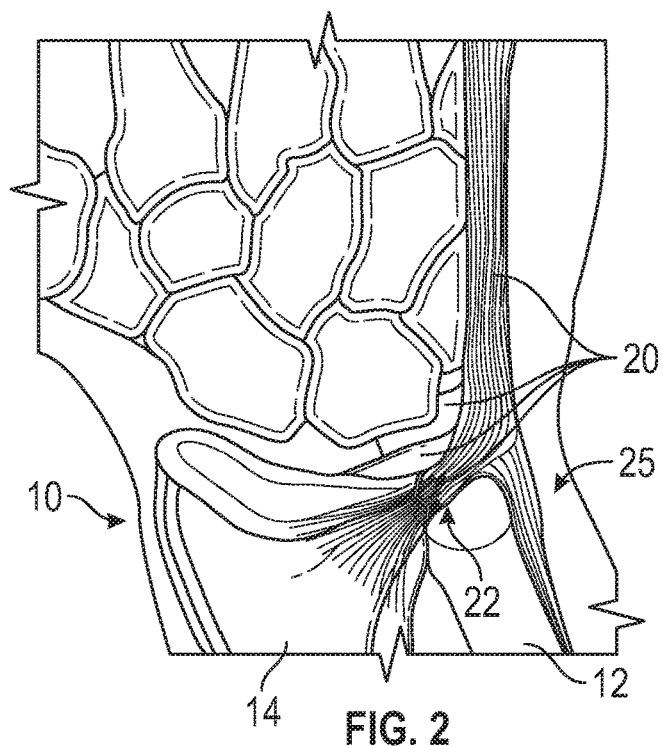
FIG. 2 illustrates a triangular fibrocartilage complex (TFCC) of a distal radioulnar joint of the wrist of FIG. 1.

Referring now to FIGS. 1 and 2, the wrist 10 includes a triangular fibrocartilage complex (TFCC) 20. The TFCC 20 is a group of tissue structures (e.g., ligament, tendon, cartilage, muscle, etc.) generally located on the pinky-finger side 25 of the wrist 10. The TFCC 20 serves numerous functions. For example, among the various other functions, the TFCC 20 stabilizes a distal radioulnar joint 22 of the wrist 10 and allows for articulation between the ulna 12 and the radius 14.

The distal radioulnar joint 22 may become unstable in response to a significant disruption of the TFCC 20. For example, trauma (e.g., fractures, etc.) and degenerative conditions (e.g., overuse, arthritis, etc.) can lead to irreparable loss of portions of the TFCC 20. This disclosure is therefore directed to methods for reconstructing the TFCC 20, such as in response to an irreparable tear or other injury.

FIGS. 3-32, with continued reference to FIGS. 1-2, schematically illustrate an exemplary method for reconstructing an unstable TFCC 20. As detailed below, the exemplary method may be employed to prepare, deliver and fixate a graft (see, for example, feature 64 of FIGS. 14-15) within the distal radioulnar joint 22 in a manner that restores the functionality to the TFCC 20, thereby improving the joint kinematics of the distal radioulnar joint 22. The term "joint kinematics" as used in this disclosure generally refers to the manner in which the bones and surrounding soft tissue of a joint interact with one another during motion.

The method of FIGS. 3-32 may be performed as an arthroscopic procedure by working through various arthroscopic portals. Alternatively, the exemplary method could be performed as an open procedure.

FIGS. 3-32 illustrate, in sequential order, an exemplary embodiment for performing a method for reconstructing the TFCC 20. Fewer or additional steps than are recited below could be performed within the scope of this disclosure. In addition, the recited order of steps shown in FIGS. 3-32 is not intended to limit this disclosure.

Figure 3:
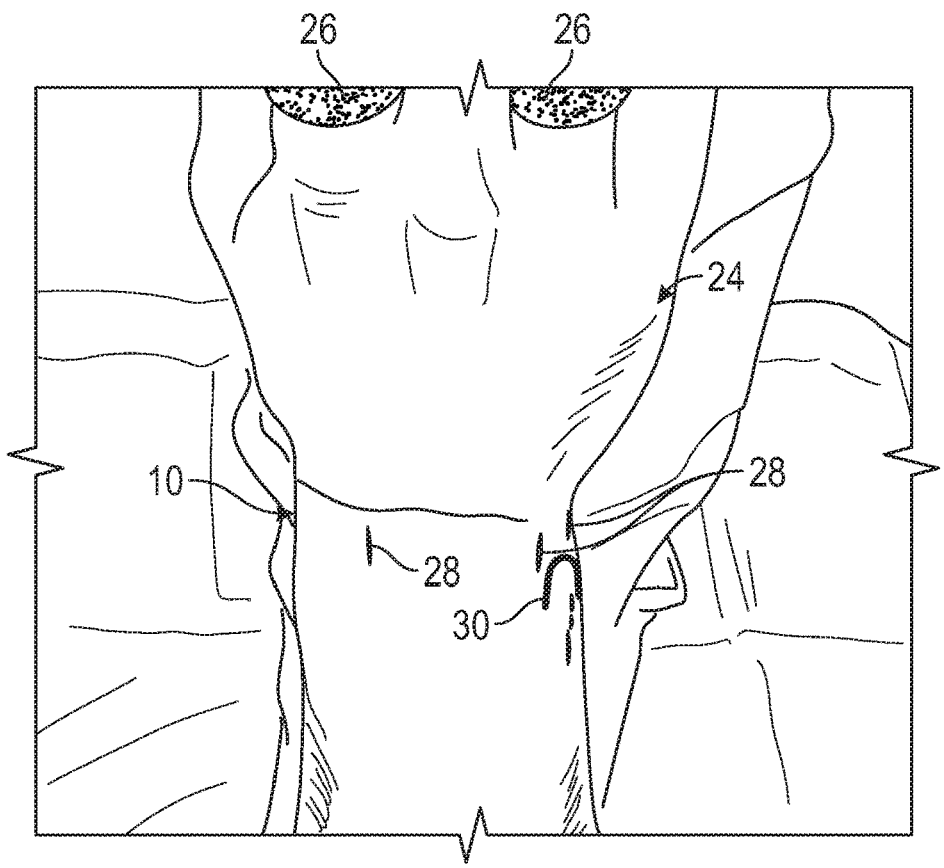
FIG. 3 schematically illustrates the positioning of a patient's hand in preparation for reconstructing the patient's TFCC.

Referring first to FIG. 3, the method may begin by positioning the patient in a supine position and positioning a hand 24 of the patient in hanging position by securing fingers of the hand 24 within fingertraps 26. Counter-traction may optionally be performed to obtain up to ten pounds of longitudinal distraction between the bones of the radiocarpal joint 18. The wrist 10 of the hand 24 may be marked with various markings 28 to indicate the locations for establishing arthroscopic portals. The locations of the markings 28, and thus the arthroscopic portals, may be selected based surgeon preference. An additional marking 30 may be drawn to indicate the location of the styloid process of the ulna 12.

Figure 4:
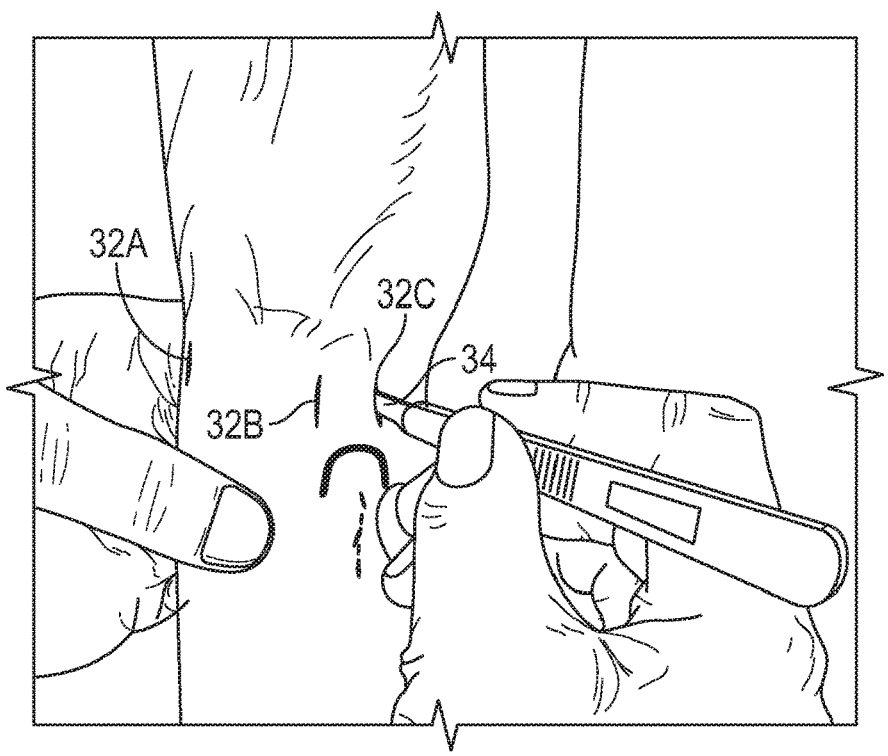
FIG. 4 schematically illustrates incisions for positioning arthroscopic portals within a wrist.

FIG. 4 illustrates the formation of several skin incisions in preparation for establishing various arthroscopic portals. A first incision 32A may be made on the radial side of the wrist 10, and a second incision 32B and a third incision 32C may be made on the ulnar side of the wrist 10. A cutting device 34, such as a scalpel, can be used to make the incisions 32A, 32B, and 32C.

Figure 5:
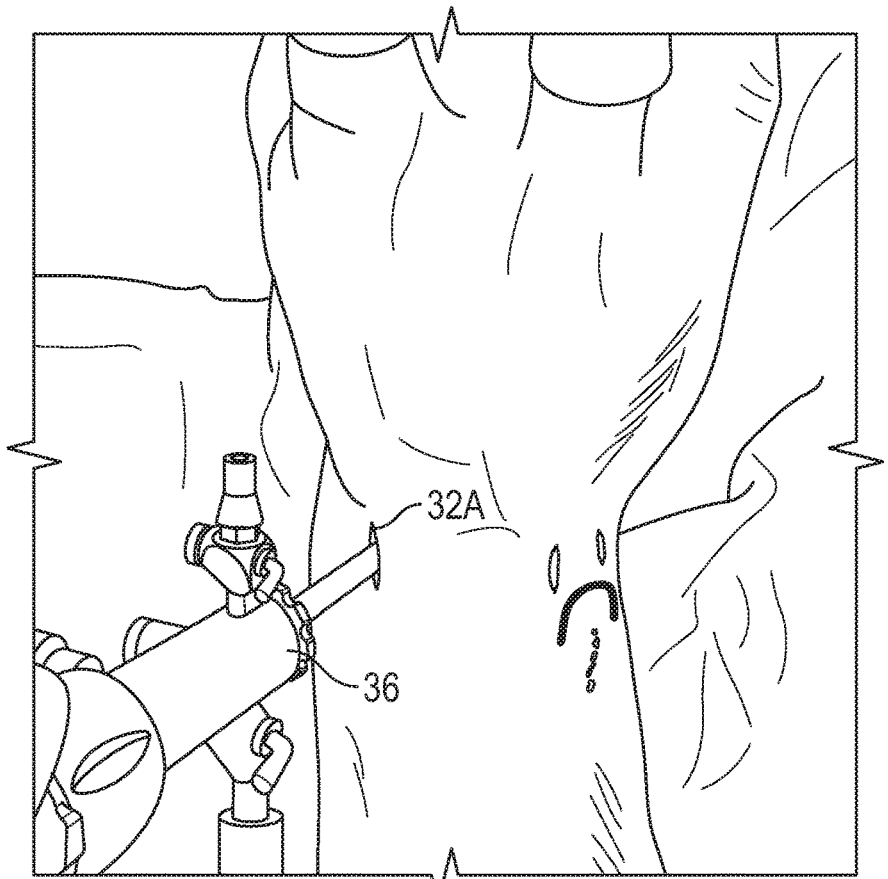
FIG. 5 schematically illustrates the positioning of a arthroscope for visualizing the distal radioulnar joint of the wrist.

An arthroscope 36 or some other imaging device may be inserted into the first incision 32A (see FIG. 5). The arthroscope 36 may be positioned according to surgeon preference for visualizing, such as via one or more arthroscopic windows, the distal radioulnar joint 22.

Upon visualizing and accessing the TFCC 20, the TFCC 20 may be debrided for better exposing the head of the ulna 12 and the ulnar side of the distal portion of the radius 14. Optionally, the dorsal and volar corners of the ulnar side of the distal radius 14 may be prepared for the surgical procedure by creating a bleeding bone bed in order to maximize vascular channels, etc. For example, a manual or mechanical pick (e.g., Arthrex's PowerPick™) may be used to create channels (bone vents) between the marrow and the cortical surface of the distal radius 14, particularly at the dorsal and volar corners of the ulnar side of the distal radius 14. This procedure serves to enhance access of growth factors and mesenchymal stem cells to the healing interface between the graft that is to be implanted (as detailed below) and the bones of the wrist 10.

Figure 6:
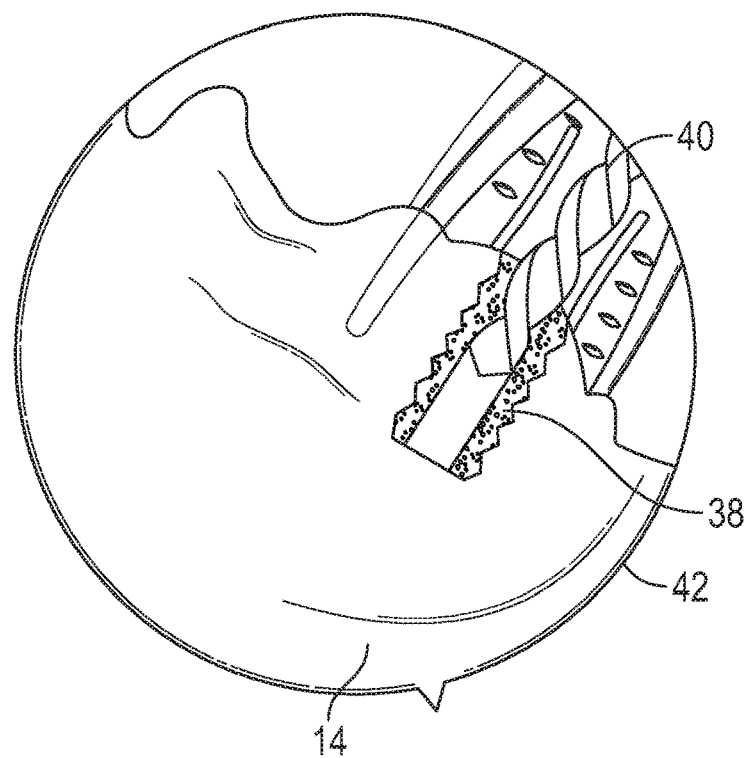
FIG. 6 schematically illustrates an arthroscopic window for visualizing the formation of bone holes in the radius.

Referring now to FIG. 6, a bone hole 38 may optionally be pre-formed at each of the dorsal corner and the ulnar corner of the ulnar side of the distal radius 14. Each bone hole 38 is sized to receive one suture anchor (as further detailed below). A drill bit 40 or other tool may be used to form the bone holes 38. The placement of the drill bit 40 relative to the radius 14 may be visualized on an arthroscopic window 42 generated by the arthroscope 36.

Figure 7:
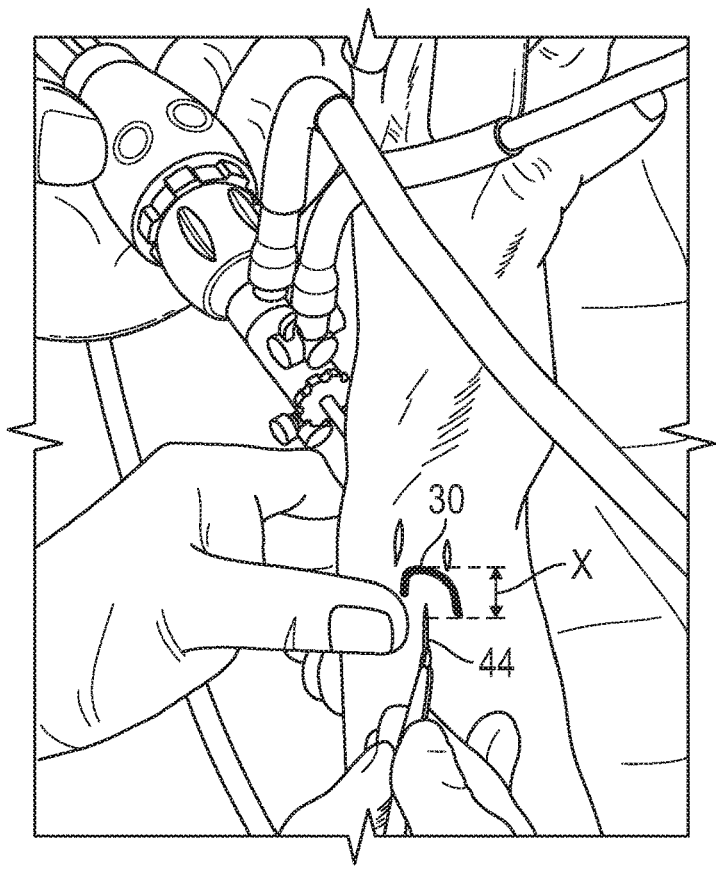
FIG. 7 schematically illustrates the formation of an incision at a location proximal to the styloid process of the ulna.

FIG. 7 illustrates the formation of an additional incision 44. The incision 44 may be made proximally of the marking 30 that indicates the location of the styloid process of the ulna 12. The incision 44 may be started at a distance X from the marking 30. In an embodiment, the distance X is approximately 1.5 cm. However, the exact distance may vary depending on the size of the patient's ulna, among other factors.

Figure 8:
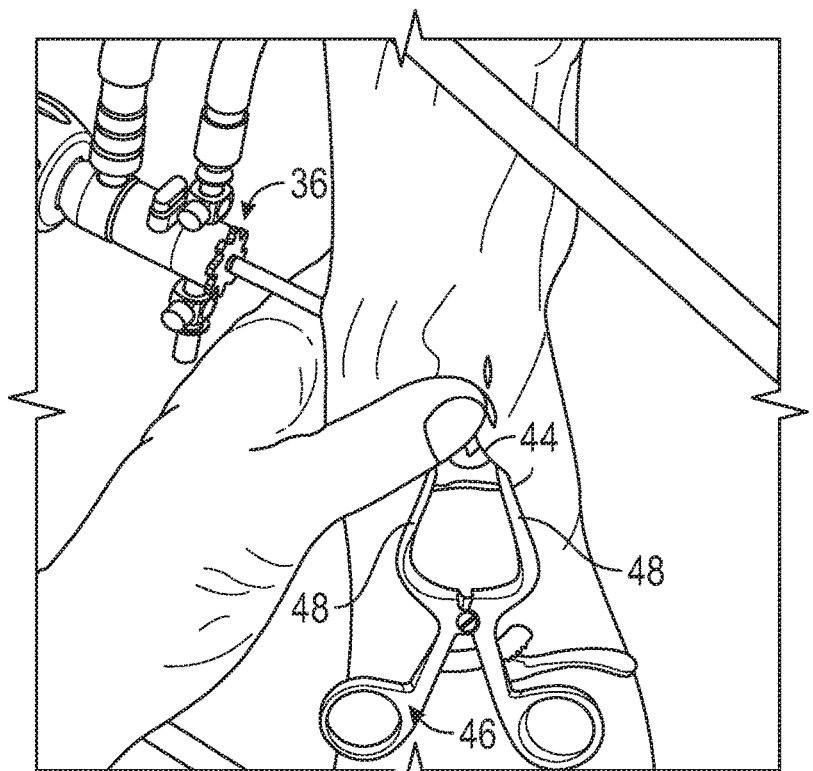
FIG. 8 schematically illustrates the use of a distractor for distracting tendons and nerves within the wrist.

Next, as shown in FIG. 8, a distractor 46 may be used to move various tendons and nerves out of the way so as to protect these tendons and nerves during the surgical procedure. The distractor 46 may be positioned within the incision 44 and then its legs 48 may be spread apart in order to distract the tendons and nerves. Spreading the legs 48 enlarges the opening formed by the incision 44, thereby increasing the amount of available work space.

Figure 9:
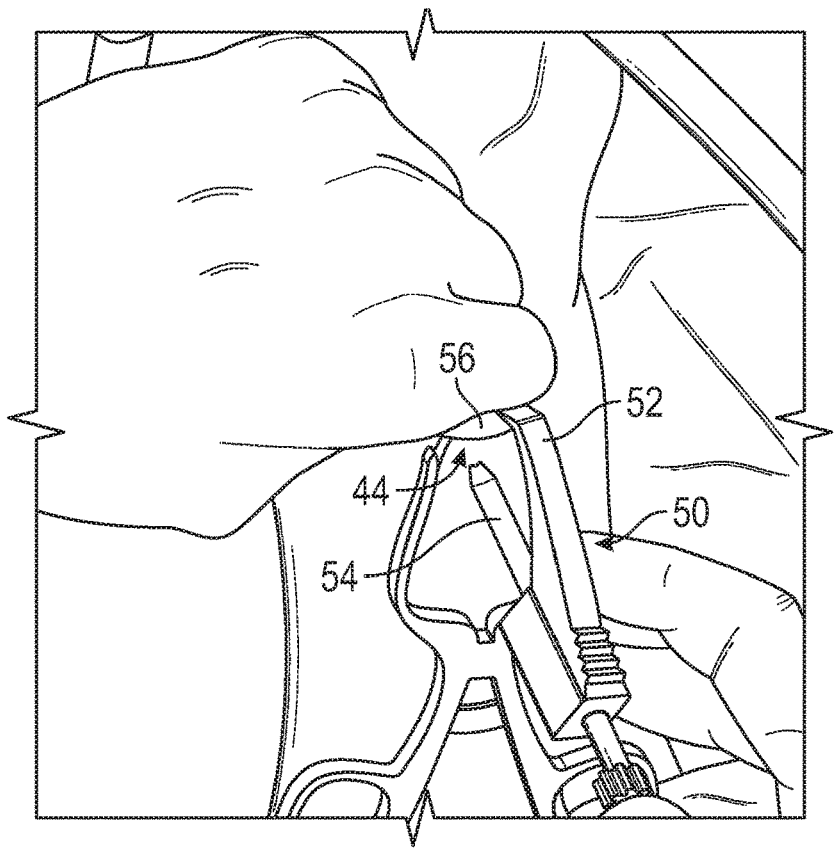
FIG. 9 schematically illustrates the positioning of a C-guide for forming a bone tunnel through the ulna.
Figure 10:
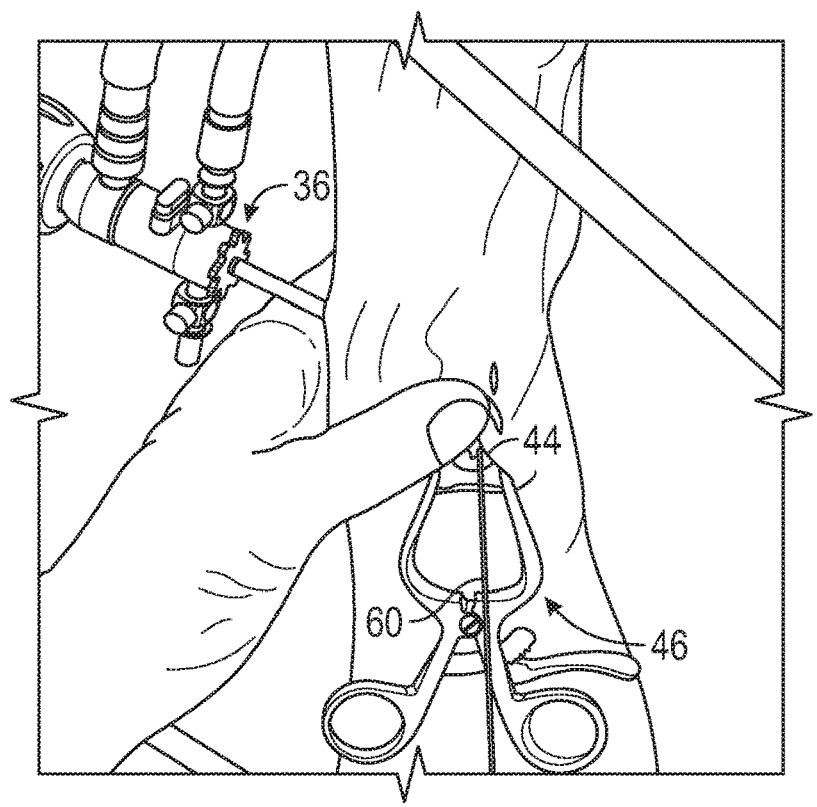
FIG. 10 schematically illustrates the placement of a guidewire within the ulna.
Figure 11:
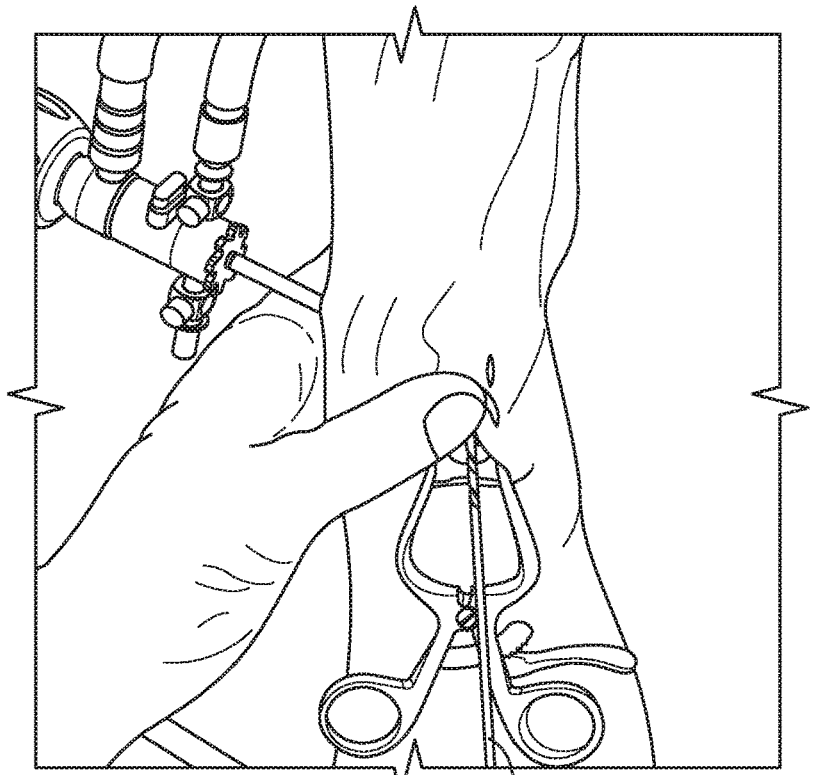
FIG. 11 schematically illustrates over-drilling the guidewire of FIG. 10.

FIG. 9 illustrates the positioning of a C-guide 50 for forming a bone tunnel (see feature 100 of FIG. 32) through the ulna 12. As further described below, the bone tunnel formed through the ulna 12 can accommodate sutures for fixating a graft relative to the ulna 12. The C-guide 50 may include a targeting prong 52 and a cannula 54. The targeting prong 52 may be introduced into the distal radioulnar joint 22 through an arthroscopic cannula 56 that may be positioned within either the second incision 32B or the third incision 32C. The targeting prong 52 may then be maneuvered into place over the ulnar fovea. A distal end 58 of the cannula 54 may be inserted through the incision 44 until it abuts against a lateral cortex of the ulna 12.

Using arthroscopic assistance, the C-guide 50 may then be used to place a guidewire 60 (see FIG. 10) from the lateral cortex of the ulna 12 through the ulnar fovea. The guidewire 60 may be over-drilled with a cannulated drill bit 62 (see FIG. 11) in order to form the bone tunnel within the ulna 12.

Figure 12:
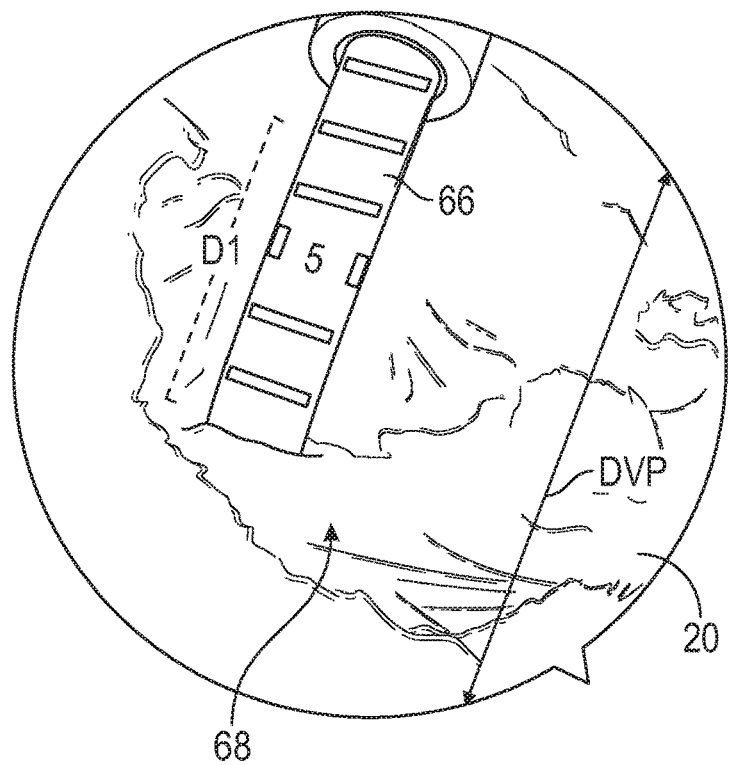
FIGS. 12 and 13 schematically illustrate the measurement of various dimensions of a defect of the TFCC. The measurements are used to size a graft.
Figure 13:
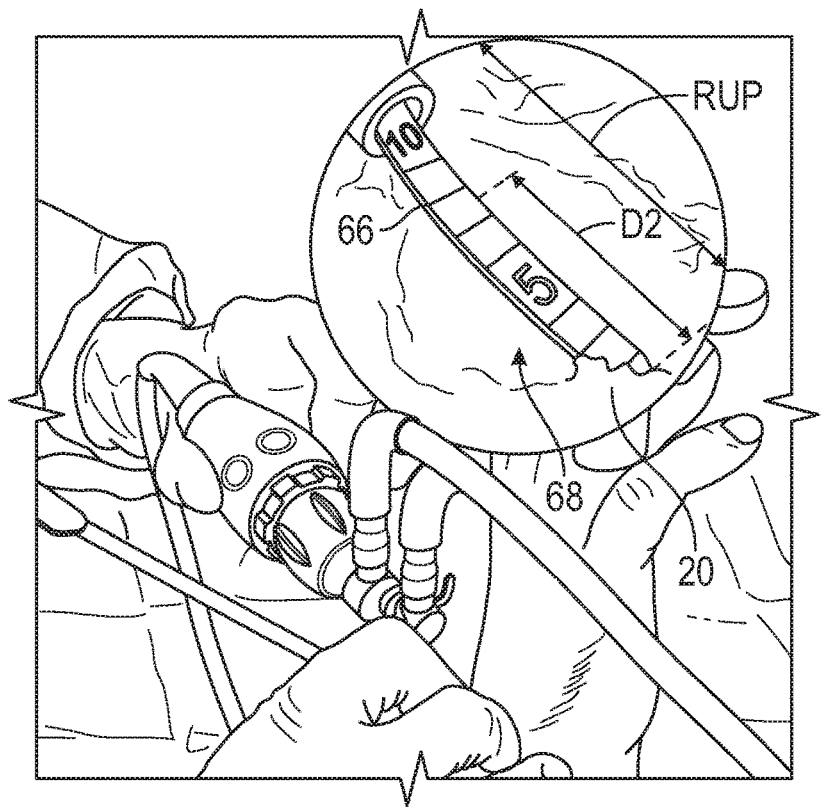
Figure 14:
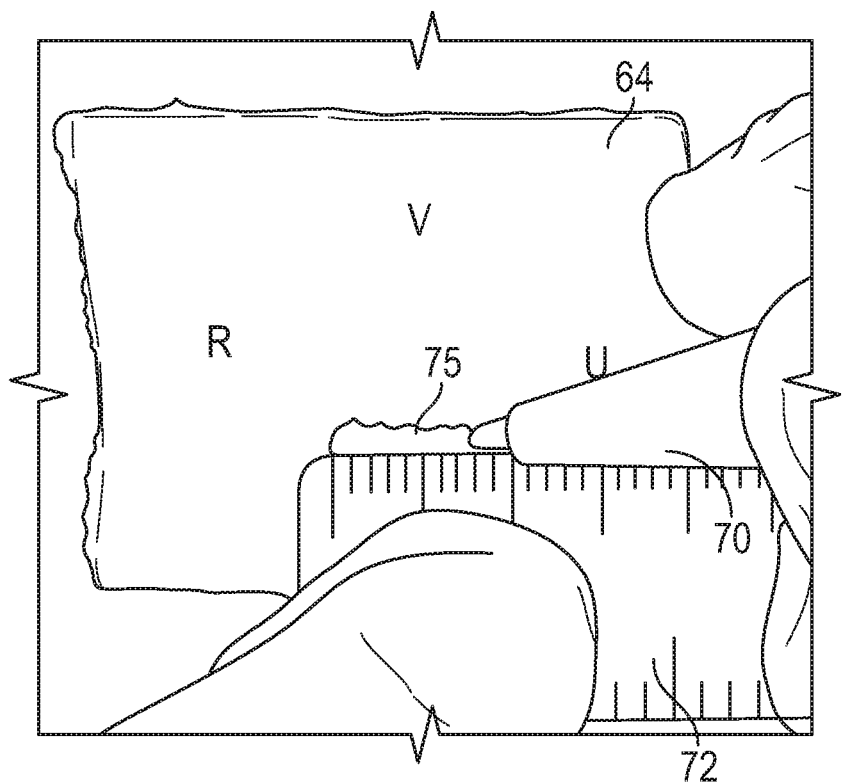
FIGS. 14 and 15 schematically illustrate the preparation of a graft for subsequent use to reconstruct defective portions of the TFCC.
Figure 15:
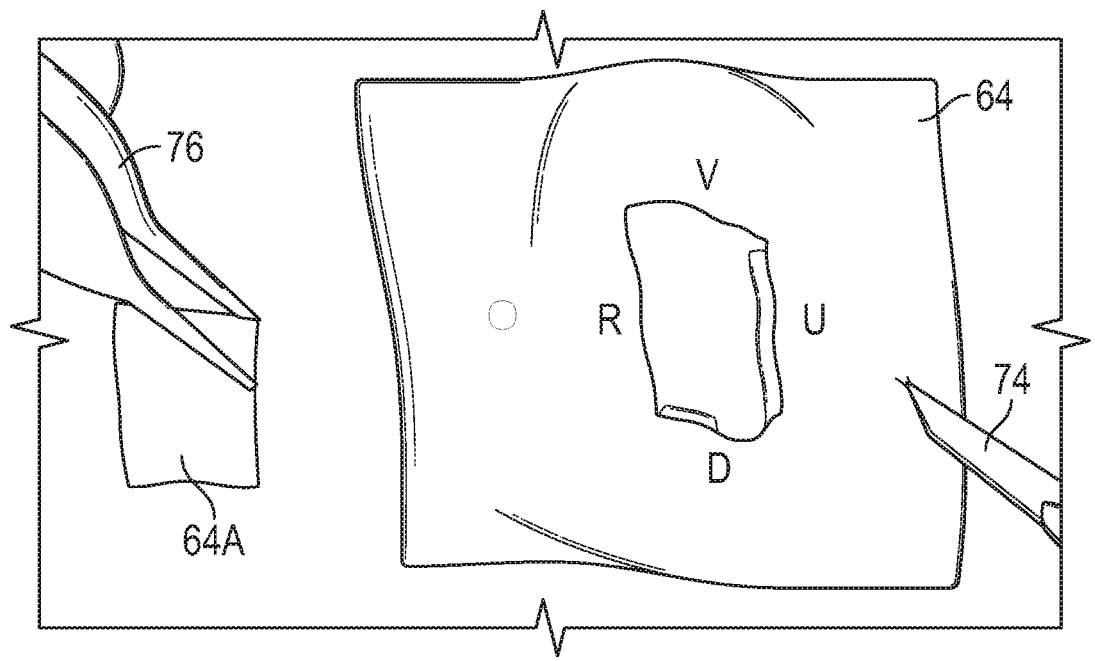

Referring now to FIGS. 12 and 13, multiple measurements may be taken in preparation for sizing and preparing a graft, which is shown as feature 64 in FIGS. 14-15, for subsequent use to reconstruct portions of the TFCC 20. A measuring probe 66 may be utilized to take each of measurements and may be positioned within the distal radioulnar joint 22 under arthroscopic assistance. In an embodiment, at least two measurements are made for sizing the graft 64. For example, the size of a defect 68 of the TFCC 20 may be measured in both a dorsal-volar plane DVP (see FIG. 12) and a radial-ulnar plane RUP (see FIG. 13) using the measuring probe 66. A first dimension D1 of the defect 68 may be measured in the dorsal-volar plane DVP, and a second dimension D2 of the defect 68 may be measured in the radial-ulnar plane RUP. It should be understood that additional measurements could be taken and recorded for sizing the graft 64 within the scope of this disclosure.

FIGS. 14-15 illustrate the preparation of the graft 64. Once prepared, the graft 64 can be used to reconstruct the defect 68 of the TFCC 20. The graft 64 could include either an allograft or an autograft. In an embodiment, the graft 64 is an acellular dermal extracellular matrix. ArthroFlex®, sold by Arthrex, Inc., is one type of dermal graft suitable for reconstructing the defect 68 of the TFCC 20.

Referring first to FIG. 14, the graft 64 may be sized using a marking pin 70 and a ruler 72. The graft 64 is sized based on the previously obtained measurements (e.g., dimensions D1 and D2). The ruler 72 is used to measure each of the dimensions D1 and D2 on the graft 64, and the marking pin 70 is used to draw lines 75 that represent the dimensions D1 and D2.

Prior to marking the dimensions D1 and D2 on the graft 64, the marking pin 70 may be used to label the radial R, ulnar U, volar V, and dorsal D sides of the graft 64. This can help with achieving the proper orientation of the graft 64 and with suture management during later steps of the method.

Next, as shown in FIG. 15, a cutting device 74 can be used to cut the graft 64 into the desired size and shape. The cutting device 74 may be a scalpel, scissors, or any other suitable cutting device. The sized graft 64A can be removed from the remaining graft material using tweezers 76.

Figure 16:
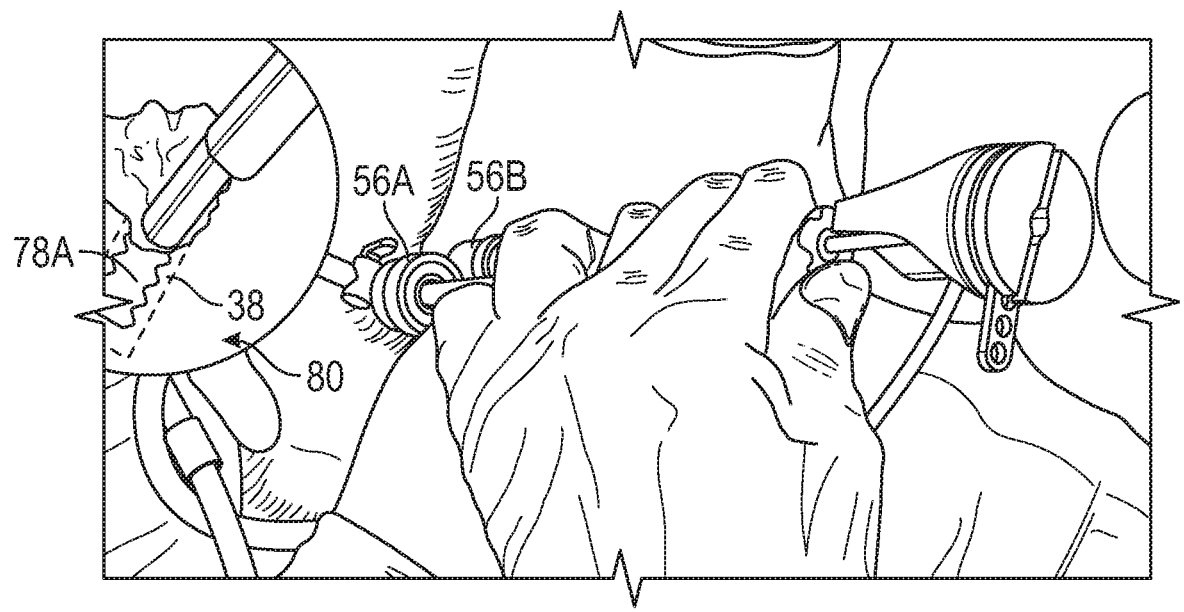
FIGS. 16 and 17 schematically illustrate the insertion of suture anchors into the ulnar side of the distal radius.
Figure 17:
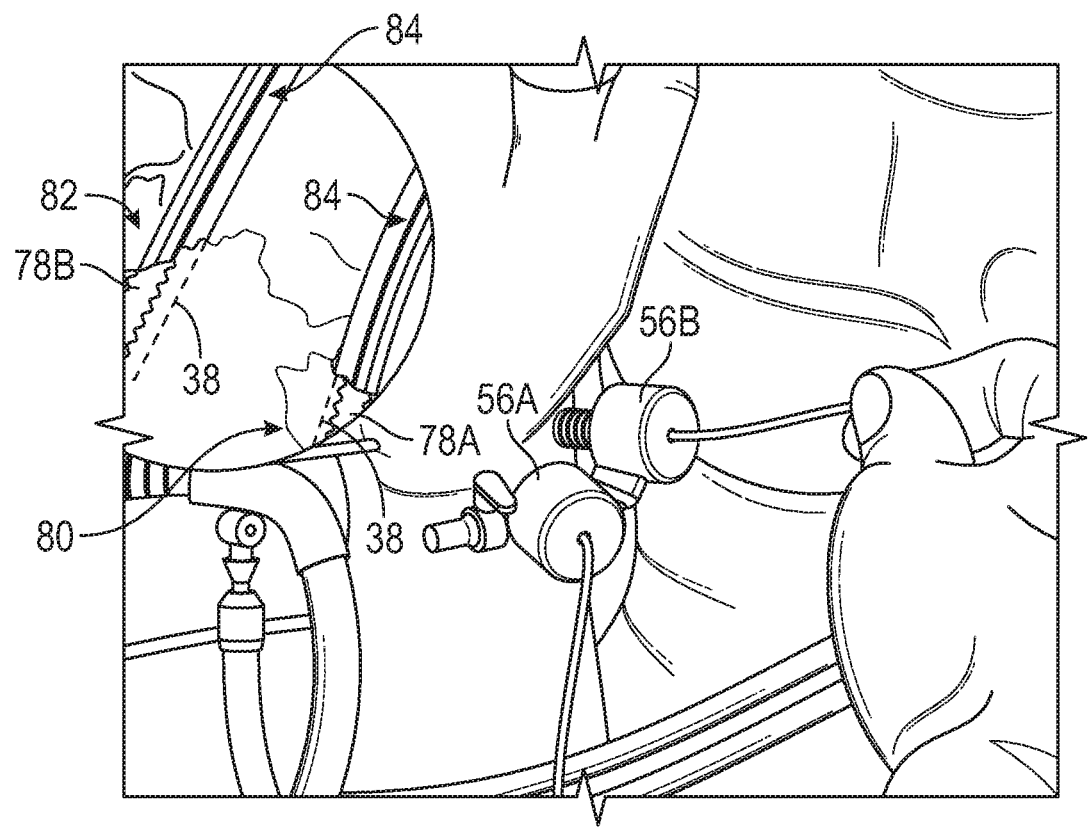
Figure 18:
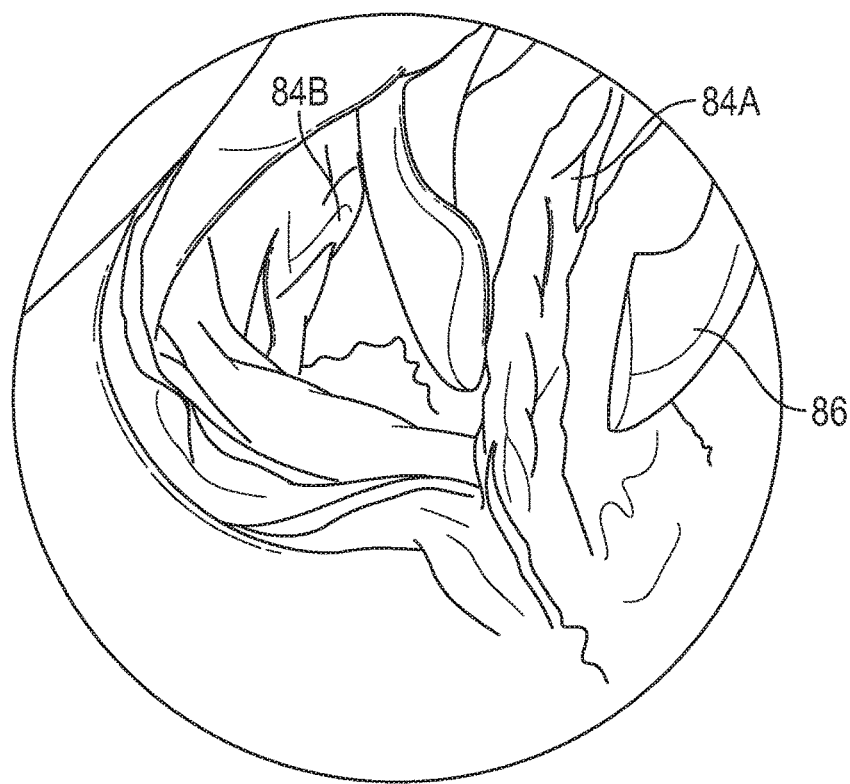
FIGS. 18 and 19 schematically illustrate the retrieval of suture strands from a first suture anchor implanted within the distal radius.
Figure 19:
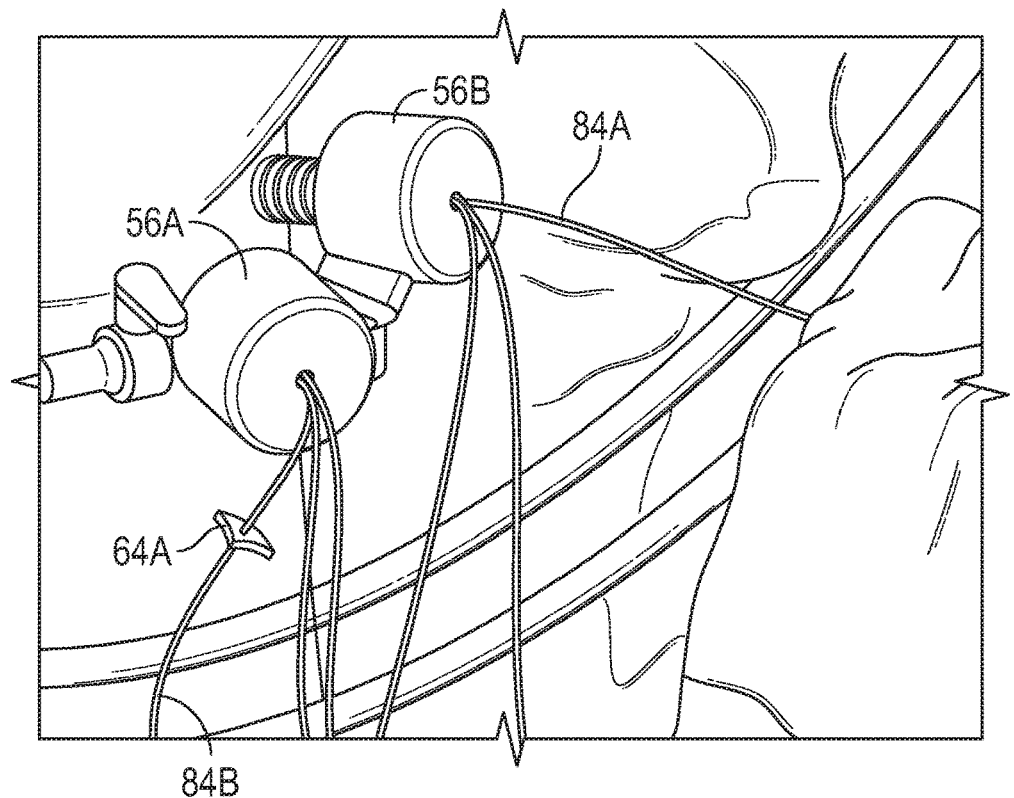
Figure 20:
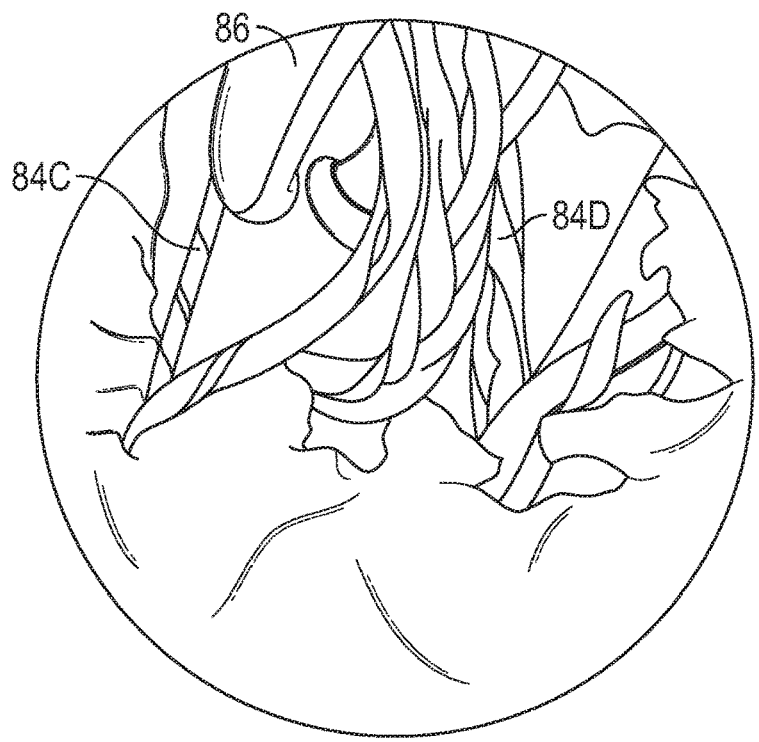
FIGS. 20 and 21 schematically illustrate the retrieval of suture strands from a second suture anchor implanted within the distal radius.
Figure 21:
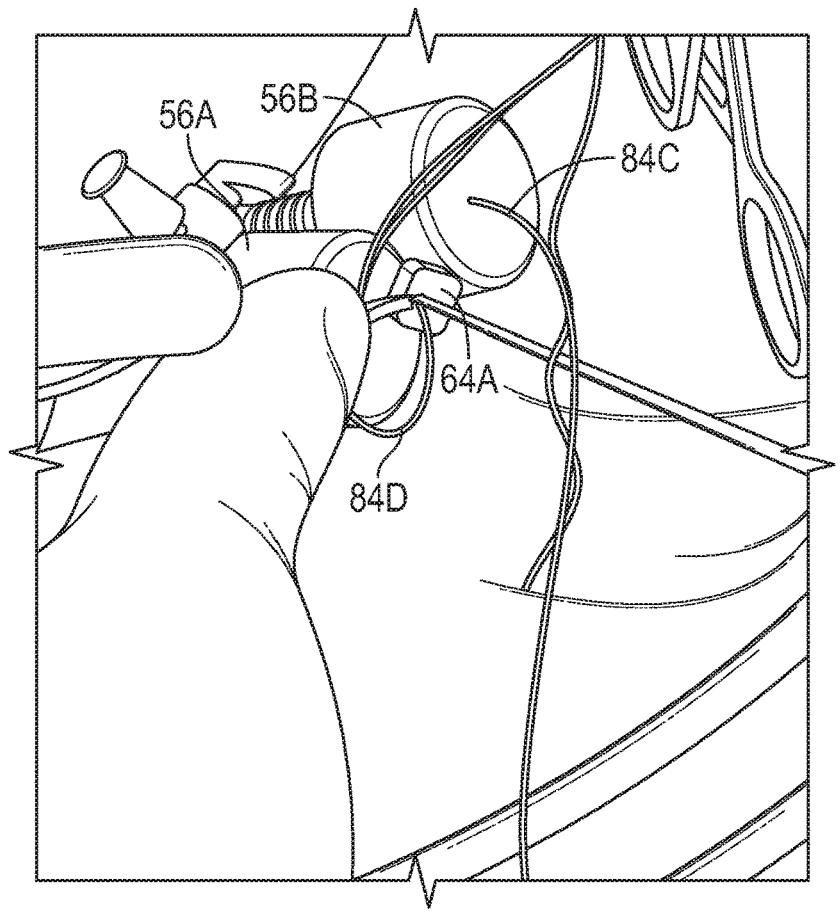

FIGS. 16 and 17 illustrate the insertion of a first suture anchor 78A and a second suture anchor 78B into the bone holes 38 previously prepared at the ulnar side of the distal radius 14. A first arthroscopic cannula 56A may be positioned within the second incision 32B and a second arthroscopic cannula 56B may be positioned within the third incision 32C prior to implanting the first and second suture anchors 78A, 78B. In an embodiment, the first suture anchor 78A is implanted near a dorsal corner 80 of the ulnar side of the distal radius 14 using the first arthroscopic cannula 56A, and the second suture anchor 78B is implanted near a volar corner 82 of the ulnar side of the distal radius 14 using the second arthroscopic cannula 56B. Although the implantation of two suture anchors is shown in this embodiment, it should be understood that additional suture anchors could be implanted as necessary to achieve sufficient graft-to-bone fixation.

In an embodiment, the first suture anchor 78A and the second suture anchor 78B are knotless suture anchors. Therefore, the first and second suture anchors 78A, 78B are capable of securing the sized graft 64A near the dorsal corner 80 and the volar corner 82 of the ulnar side of the distal radius 14 without tying knots over the graft 64. Knotless SutureTak® Anchor, sold by Arthrex, Inc., is one type of knotless suture anchor that can be used to knotlessly secure the sized graft 64A.

Each of the first and second suture anchors 78A, 78B may carry one or more sutures 84. The sutures 84 may include individual suture strands, multiple suture strands, suture tape, or any other flexible strand or suture-like product. Therefore, once the suture anchors 78A and 78B have been implanted, the sutures 84 are fixated at desired locations within the distal radius 14. In other words, the suture anchors 78A, 78B mark the fixation locations of the sutures 84.

FIGS. 18-26 illustrate additional steps of the exemplary method for reconstructing the TFCC 20. The sized graft 64A may be aligned and oriented at a location external to, or outside of, the distal radioulnar joint 22 in a manner that mimics its implanted position.

A shuttle suture strand 84A (see FIG. 18) of the sutures 84 of the first suture anchor 78A may first be retrieved through the second arthroscopic cannula 56B (see FIG. 19) using a suture retriever 86. KingFisher® retriever, sold by Arthrex, Inc., is one type of suture retriever that could be used.

Next, a stay suture strand 84B of the sutures 84 of the first suture anchor 78A may be retrieved through the first arthroscopic cannula 56A. The stay suture strand 84B may then be passed through the sized graft 64A while the sized graft 64A is located outside of the distal radioulnar joint 22 (see FIG. 19). The stay suture strand 84B may be passed through the portion of the sized graft 64A that corresponds to the dorsal corner 80 of the ulnar side of the distal radius 14.

A shuttle suture strand 84C (see FIG. 20) of the sutures 84 of the second suture anchor 78B may also be retrieved through the second arthroscopic cannula 56B using the suture retriever 86. Similarly, a stay suture strand 84D of the sutures 84 of the second suture anchor 78B may be retrieved through the first arthroscopic cannula 56A. The stay suture strand 84D may then be passed through the sized graft 64A while the sized graft 64A is still located outside of the distal radioulnar joint 22 (see FIG. 21). The stay suture strand 84D may be passed through the portion of the sized graft 64A that corresponds to the volar corner 82 of the ulnar side of the distal radius 14.

Figure 22:
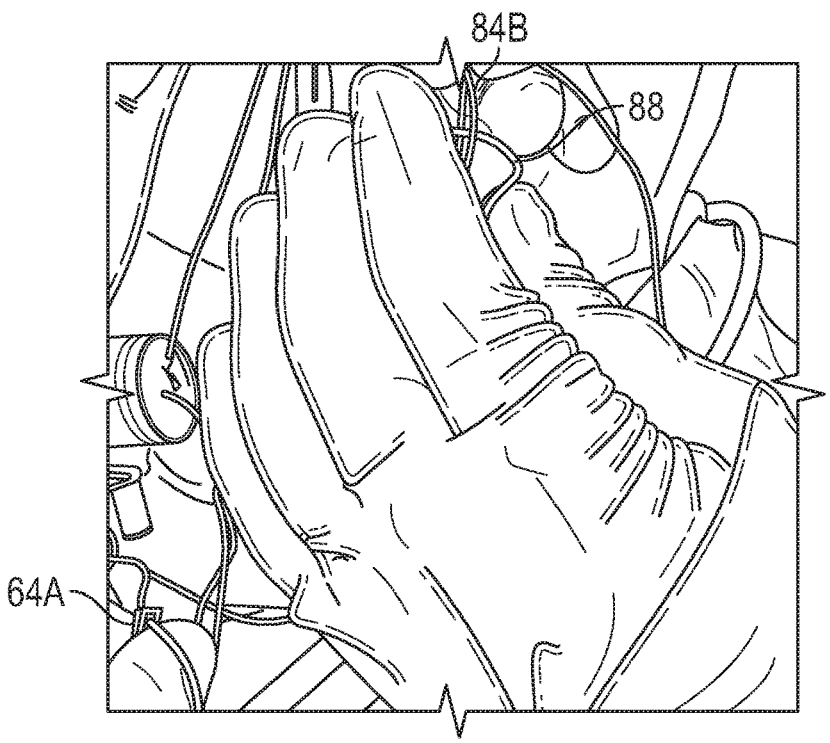
FIG. 22 schematically illustrates loading a stay suture stand through a loop of a shuttle suture strand.
Figure 23:
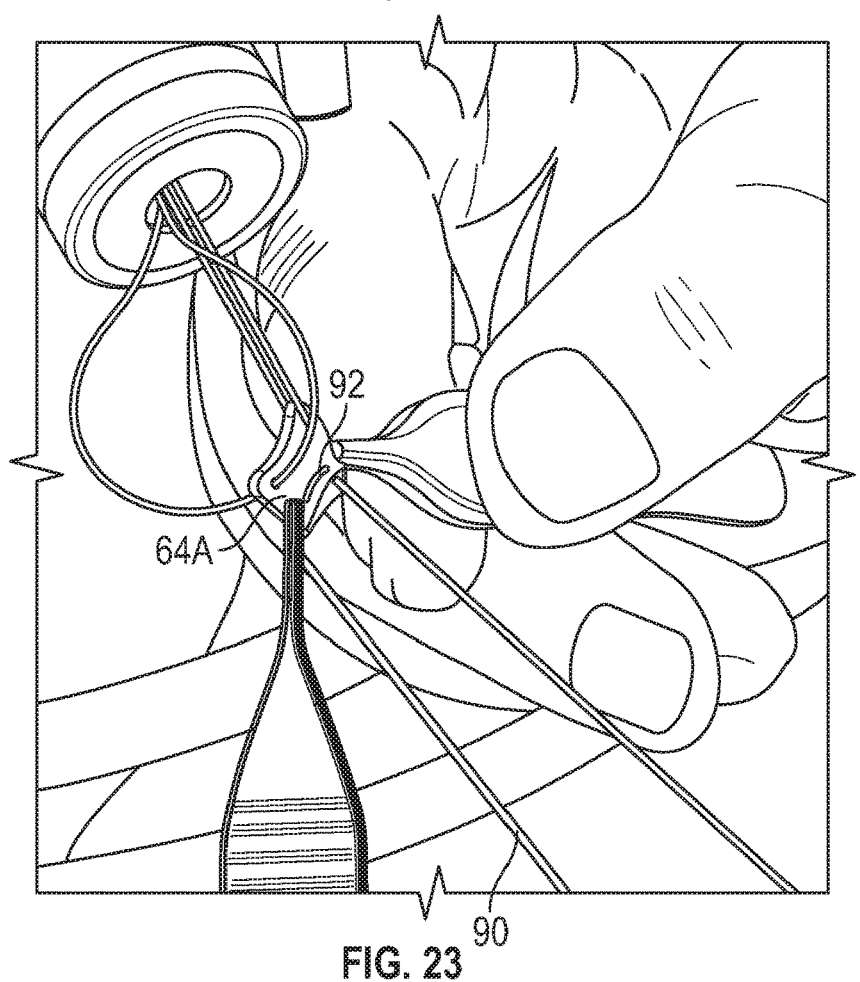
FIG. 23 schematically illustrates attaching a suture to a sized graft.

Next, as shown in FIG. 22, the stay suture stand 84B may be loaded through a loop 88 of the shuttle suture strand 84A. In a similar fashion, the stay suture strand 84D may be loaded through a loop of the shuttle suture stand 84C. Moreover, as shown in FIG. 23, an additional suture 90 may be connected to the ulnar side of the sized graft 64A via a mattress stitch 92.

Figure 24:
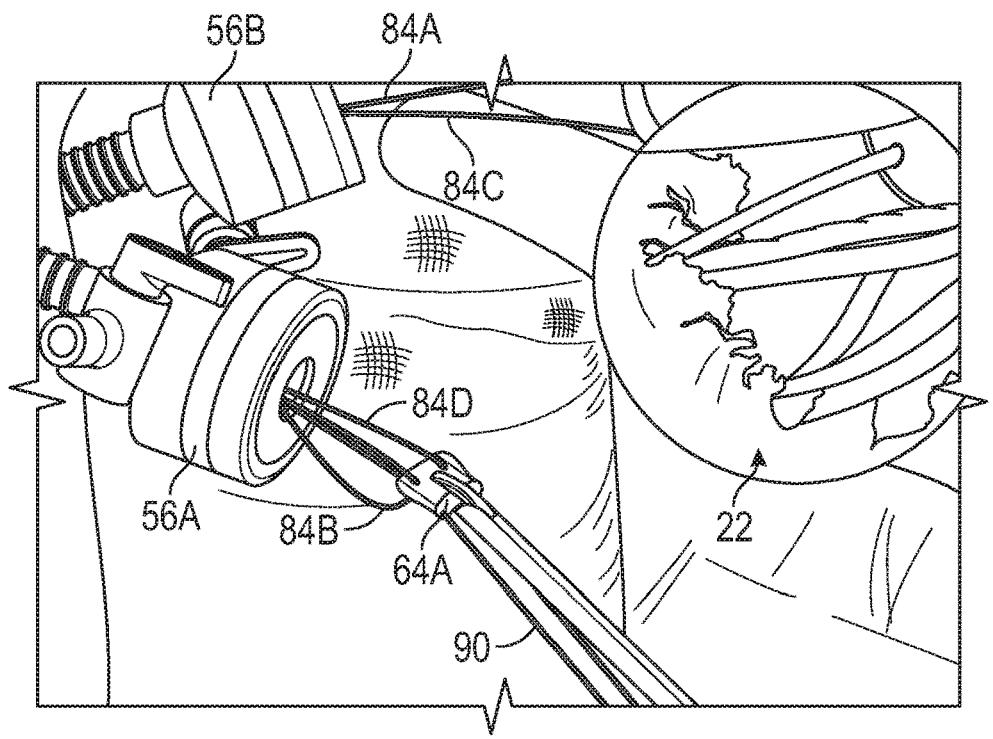
FIGS. 24 and 25 schematically illustrate shuttling the sized graft into the distal radioulnar joint.
Figure 25:
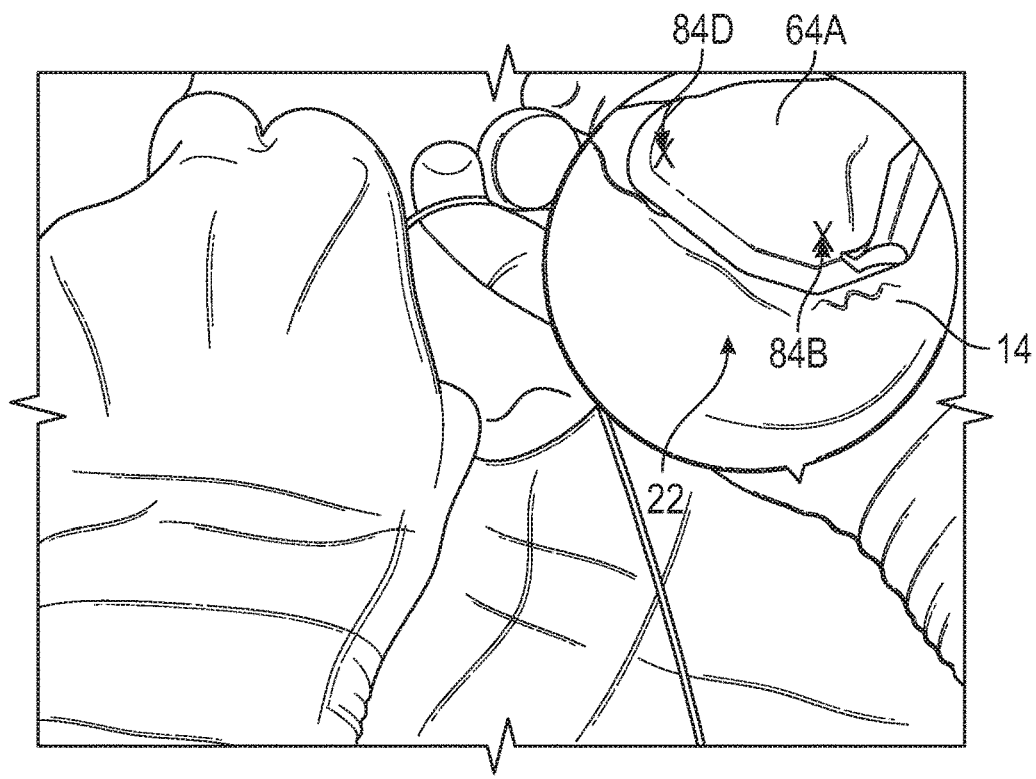
Figure 26:
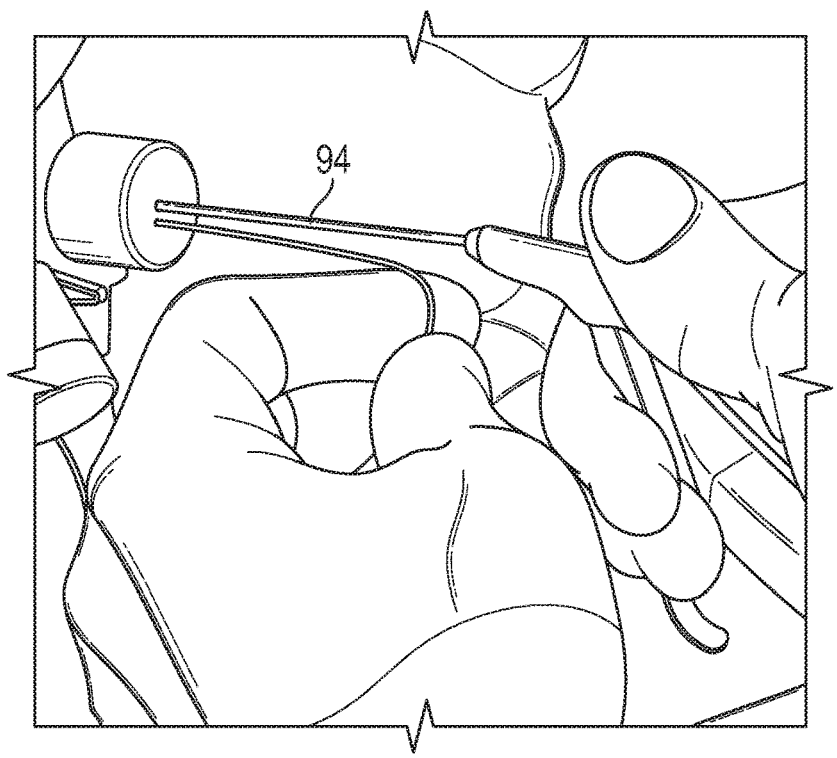
FIG. 26 schematically illustrates cutting stay sutures from suture anchors.

Referring now to FIGS. 24-25, the sized graft 64A may now be shuttled into the distal radioulnar joint 22. The sized graft 64A may be shuttled through the arthroscopic cannula 56A by pulling and/or toggling the shuttle suture strands 84A, 84C exiting from the arthroscopic cannula 56B in order to allow the stay suture strands 84B and 84D to be spliced through themselves at a location inside the anchor bodies of the first and second suture anchors 78A, 78B, thereby forming spliced loops. Tension may be applied to the shuttle suture strands 84A, 84C until an adequate amount of anatomic contact between the sized graft 64A and the ulnar side of the distal radius 14 is achieved. Thereafter, the portions of the stay suture strands 84B, 84D that extend from the suture anchors 78A, 78B may be cut with a cutting device 94 (see FIG. 26).

Figure 27:
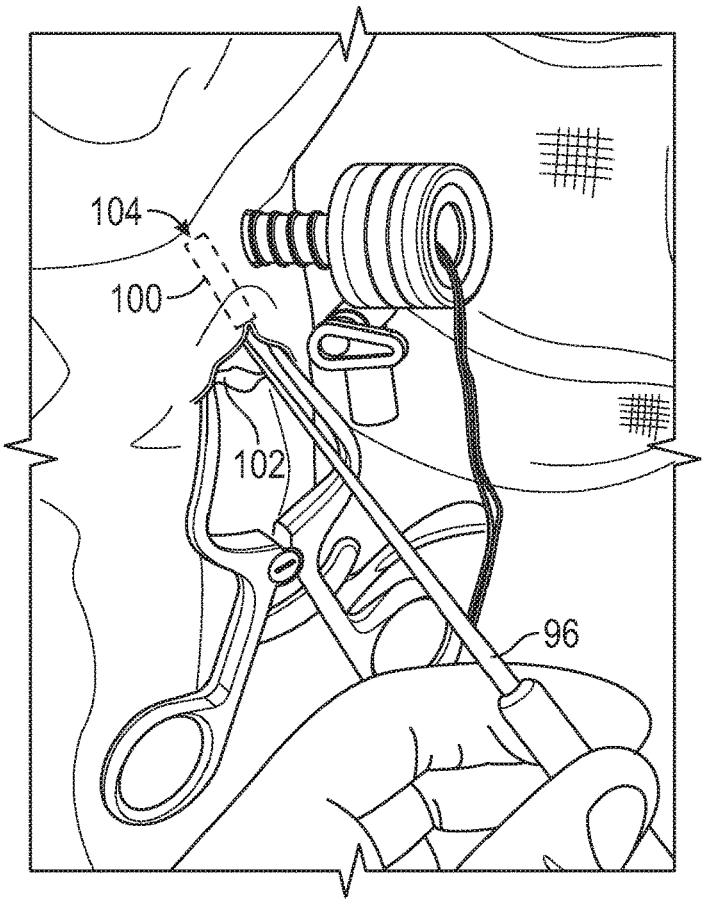
FIGS. 27, 28, 29, and 30 schematically illustrate shuttling a suture of a sized graft through a bone tunnel formed in the ulna.
Figure 28:
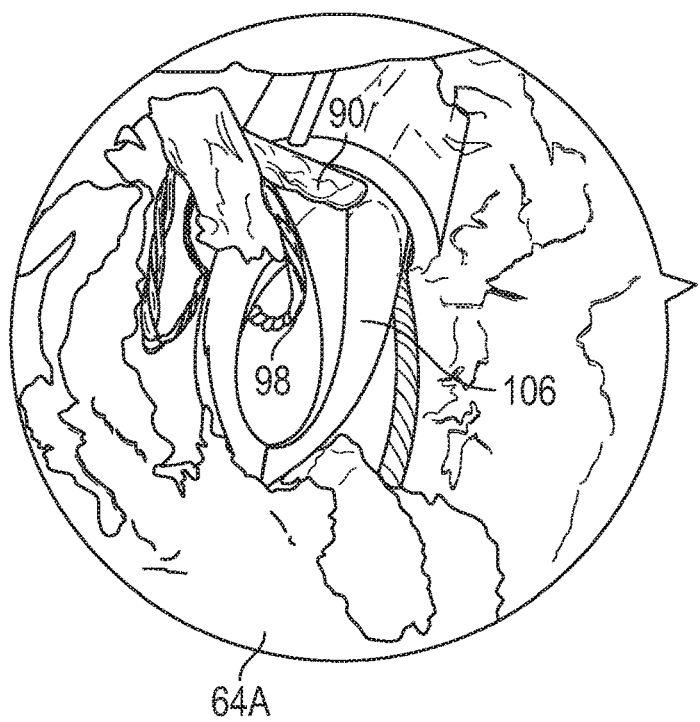
Figure 29:
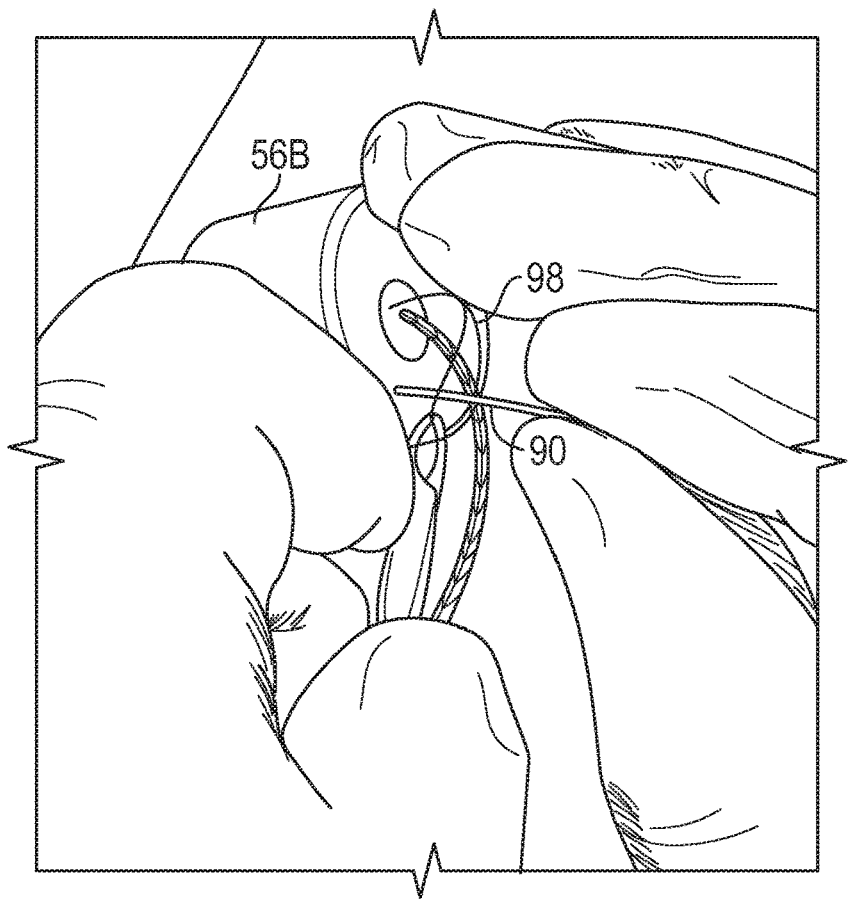
Figure 30:
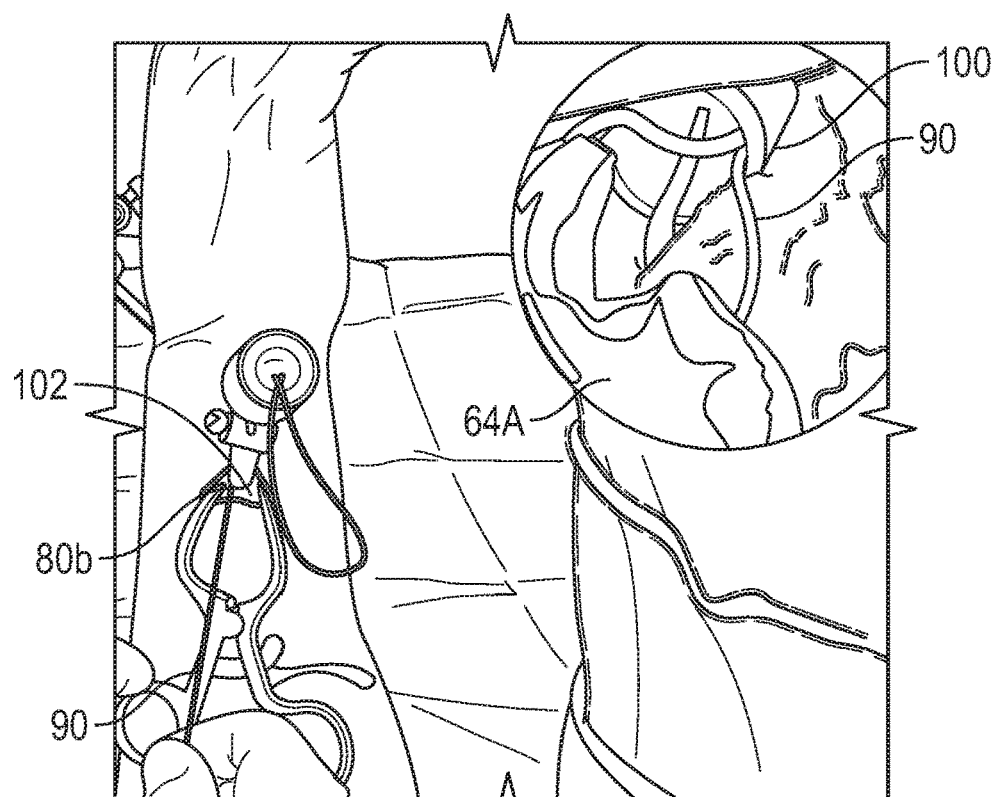

FIGS. 27-31 illustrate the remaining steps of the exemplary method for reconstructing the TFCC 20. First, as shown in FIG. 27, a suture passer 96 having a Nitinol loop 98 (best shown in FIG. 28) is passed through the bone tunnel 100 that was previously formed through the ulna 12 by the guidewire 60 and the drill bit 62 (see FIGS. 9-11). The suture passer 96 may be inserted at a lateral cortex 102 of the ulna 12 and may exit through the fovea 104 of the ulna 12.

Next, a grasper 106 (see FIG. 28) may be used to recover both the Nitinol loop 98 and the suture(s) 90 that is connected to the ulnar side of the sized graft 64A. The Nitinol loop 98 and the suture 90 may be pulled outside of the distal radioulnar joint 22 through the arthroscopic cannula 56B. The suture 90 may be threaded through the Nitinol Loop 98 (see FIG. 29) and may then be shuttled through the bone tunnel 100 until it exits from the lateral cortex 102 (see FIG. 30).

Figure 31:
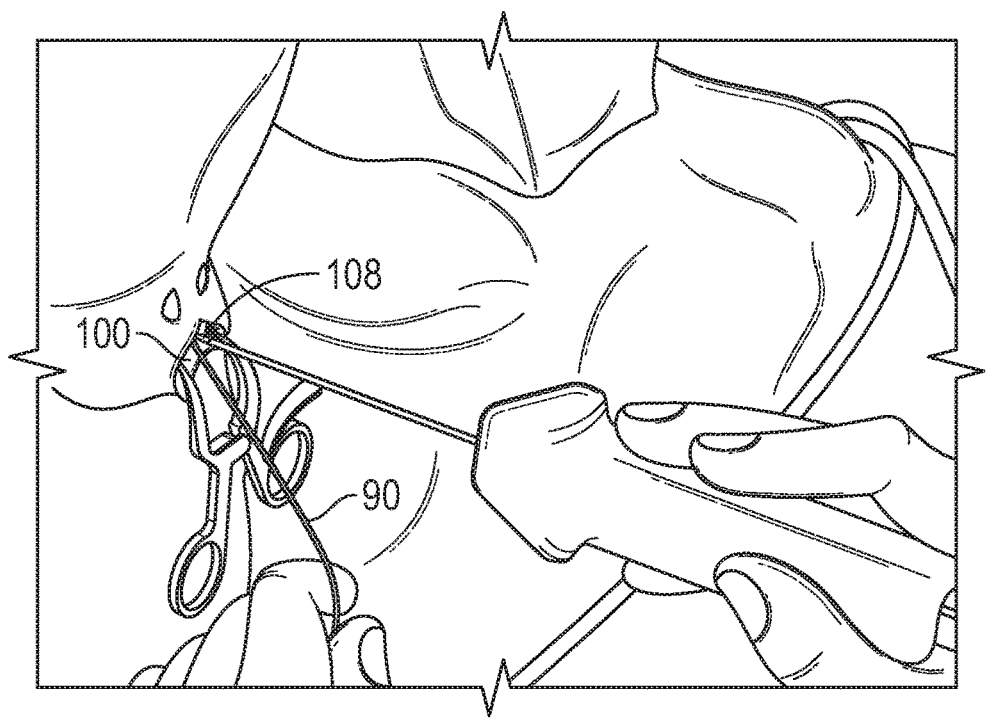
FIG. 31 schematically illustrates fixation of the suture at a lateral cortex of the ulna.

Finally, as shown in FIG. 31, the suture 90 may be fixated within the bone tunnel 100 by an additional suture anchor 108 that is inserted into the opening of the bone tunnel 100 formed at the lateral cortex 102. In an embodiment, the suture anchor 108 is a knotless suture anchor, such as a Mini PushLock® sold by Arthrex, Inc., that traps the suture 90 between the wall of the bone tunnel 100 and an anchor body of the suture anchor 108.

Figure 32:
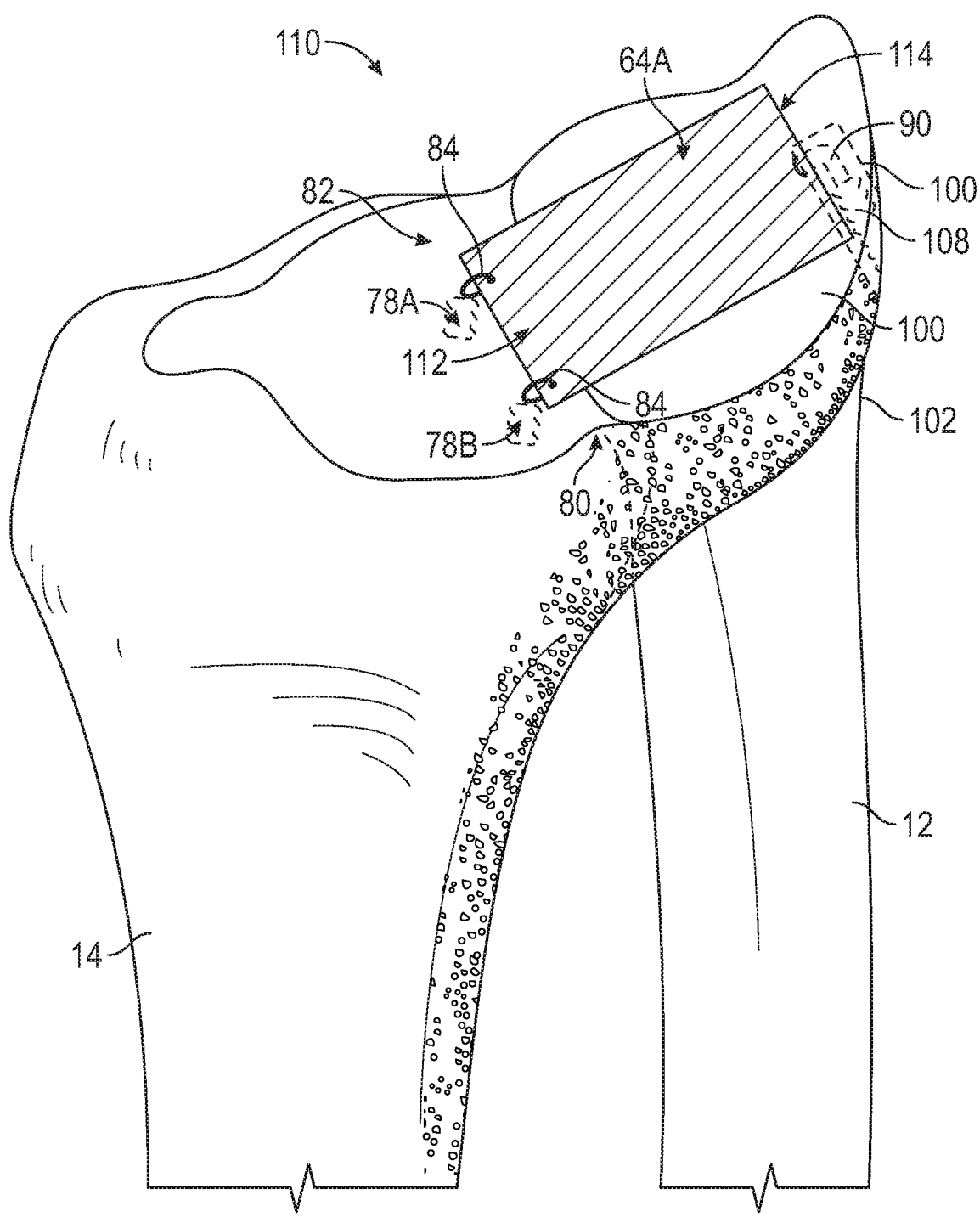
FIG. 32 schematically illustrates a final repair achieved by an exemplary method of reconstructing the TFCC.

FIG. 32 illustrates a final repair 110 achieved by performing the above method. A medial side 112 of the sized graft 64A is secured at each of the dorsal corner 80 and the volar corner 82 of the ulnar side of the distal radius 14 by the suture anchors 78A, 78B and their attached sutures 84, and a lateral side 114 of the sized graft 64 is secured to the ulna 12 via the suture 90 that is passed through the bone tunnel 100 and secured at the lateral cortex 102 of the ulna 12 by the suture anchor 108.

A kit for reconstructing the TFCC 20 can also be provided. The kit may include, for example, the materials necessary for TFCC reconstruction. In some embodiments, the kit may include:

1. At least (3) knotless suture anchors pre-loaded with suture.
2. One or more dermal allografts. The dermal allografts, or other appropriate biologically compatible material, may be provided with a suture already passed through the graft, or instead, without suture passed through the graft.
3. Disposable drills, drill guides, punches, and taps for implanting the knotless suture anchors.

Optionally, the kit could include an instructional insert with instructive diagrams and/or describing the methodology provided herein to perform a kinematic reconstruction technique, such as for a TFCC reconstruction.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A method for reconstructing a triangular fibrocartilage complex (TFCC) of a wrist, comprising:
    forming a first bone hole near a dorsal corner of an ulnar side of a radius;
    forming a second bone hole near a volar corner of the ulnar side of the radius;
    forming a bone tunnel through an ulna, wherein the bone tunnel extends from a lateral cortex of the ulna to a fovea of the ulna;
    implanting a first suture anchor in the first bone hole;
    implanting a second suture anchor in the second bone hole;
    measuring a first dimension of a defect of the TFCC in a dorsal-volar plane;
    measuring a second dimension of the defect in a radial-ulnar plane;
    subsequent to the measuring, sizing a graft to a size indicated by the first dimension and the second dimension;

retrieving a first suture strand from the first suture anchor and a second suture strand from the second suture anchor;

passing the first suture strand and the second suture strand through the sized graft with the sized graft located externally from a distal radioulnar joint of the wrist;

passing a third suture strand through the sized graft;

shuttling the sized graft into the distal radioulnar joint;

shuttling the third suture strand through the bone tunnel;

fixating the graft to the radius with the first suture strand and the second suture strand; and fixating the graft to the ulna with the third suture strand.

2. The method as recited in claim 1, wherein the graft is a dermal graft.

3. The method as recited in claim 2, wherein the dermal graft is an acellular dermal extracellular matrix graft.

4. The method as recited in claim 1, wherein the first suture anchor and the second suture anchor are knotless suture anchors.

5. The method as recited in claim 1, wherein forming the bone tunnel through the ulna includes:

making an incision at a location that is proximal to a styloid process of the ulna;

inserting a guidewire through the lateral cortex of the ulna and then through the fovea of the ulna;

over-drilling the guidewire with a drill bit to form the bone tunnel.

6. The method as recited in claim 1, wherein the measuring is performed with a measuring probe that is inserted through an arthroscopic cannula.

7. The method as recited in claim 1, wherein sizing the graft includes marking the graft to indicate the first dimension and the second dimension.

8. The method as recited in claim 1, wherein shuttling the sized graft into the distal radioulnar joint includes:

loading the first suture strand through a loop of a shuttle suture strand of the first suture anchor;

loading the second suture strand through a loop of a shuttle suture strand of the second suture anchor; and toggling the shuttle suture strands, thereby pulling the sized graft into place against the ulnar side of the radius.

9. The method as recited in claim 1, wherein passing the third suture strand through the sized graft includes:

connecting the third suture strand to the sized graft via a mattress stitch.

10. The method as recited in claim 1, wherein the third suture strand is shuttled through the bone tunnel after shuttling the sized graft into the distal radioulnar joint.

11. A method for reconstructing a triangular fibrocartilage complex (TFCC) of a wrist, comprising:

measuring a defect of the TFCC;

sizing a dermal graft to a size indicated by measuring the defect;

shuttling the sized dermal graft into a distal radioulnar joint of the wrist;

fixating the sized dermal graft to a radius with a knotless suture anchor; and fixating the graft to an ulna with an additional knotless suture anchor, wherein the additional knotless suture anchor is received within a bone tunnel that extends from a lateral cortex of the ulna to a fovea of the ulna.

12. The method as recited in claim 1, wherein the bone tunnel includes a first opening at the lateral cortex and a second opening at the fovea.

13. The method as recited in claim 12, wherein the third suture strand is fixated at the first opening but not the second opening by a third suture anchor.

14. A method for reconstructing a triangular fibrocartilage complex (TFCC) of a wrist, comprising:

forming a first bone hole near a dorsal corner of an ulnar side of a radius;

forming a second bone hole near a volar corner of the ulnar side of the radius;

forming a bone tunnel through an ulna;

implanting a first suture anchor in the first bone hole;

implanting a second suture anchor in the second bone hole;

measuring a first dimension of a defect of the TFCC in a dorsal-volar plane;

measuring a second dimension of the defect in a radial-ulnar plane;

subsequent to the measuring, sizing a graft to a size indicated by the first dimension and the second dimension;

retrieving a first suture strand from the first suture anchor and a second suture strand from the second suture anchor;

passing the first suture strand and the second suture strand through the sized graft with the sized graft located externally from a distal radioulnar joint of the wrist;

passing a third suture strand through the sized graft;

shuttling the sized graft into the distal radioulnar joint;

shuttling the third suture strand through the bone tunnel;

fixating the graft to the radius with the first suture strand and the second suture strand; and fixating the graft to the ulna with the third suture strand, wherein shuttling the third suture through the bone tunnel includes:

passing a loop through the bone tunnel in a direction from a lateral cortex of the ulna toward a fovea of the ulna;

retrieving the loop and the third suture strand through an arthroscopic cannula;

threading the third suture strand through the loop; and pulling the loop and the third suture strand through the bone tunnel in a direction from the fovea toward the lateral cortex.

15. The method as recited in claim 14, comprising:

fixating the third suture strand at the lateral cortex with a third suture anchor.

16. The method as recited in claim 15, wherein the third suture anchor is a knotless suture anchor.

17. The method as recited in claim 1, wherein sizing the graft includes:

cutting the graft to the size with a scalpel.

18. The method as recited in claim 11, wherein the bone tunnel includes a first opening at the lateral cortex and a second opening at the fovea.

19. The method as recited in claim 18, wherein a suture that is connected to the graft and the additional knotless suture anchor extends within the bone tunnel between the fovea and the lateral cortex.

20. The method as recited in claim 18, wherein the additional knotless suture anchor is received through the first opening but not through the second opening.

* * * * *